US009442094B2

(12) United States Patent
Sinha et al.

(10) Patent No.: US 9,442,094 B2
(45) Date of Patent: Sep. 13, 2016

(54) APPARATUS AND METHOD FOR ACOUSTIC MONITORING OF STEAM QUALITY AND FLOW

(75) Inventors: Dipen N. Sinha, Los Alamos, NM (US); Cristian Pantea, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 903 days.

(21) Appl. No.: 13/414,457

(22) Filed: Mar. 7, 2012

(65) Prior Publication Data

US 2013/0067992 A1    Mar. 21, 2013

Related U.S. Application Data

(60) Provisional application No. 61/449,791, filed on Mar. 7, 2011.

(51) Int. Cl.
| | | |
|---|---|---|
| G01N 29/36 | (2006.01) | |
| G01F 1/66 | (2006.01) | |
| G01N 29/036 | (2006.01) | |

(52) U.S. Cl.
CPC ............. *G01N 29/036* (2013.01); *G01F 1/666* (2013.01)

(58) Field of Classification Search
CPC ..................... G01N 29/036; G01N 2291/014; G01N 2291/02836; G01N 29/14; G01N 2291/017; G01N 2291/02425; G01N 2291/02433; G01N 25/60; G01N 29/12; G01N 29/42; G01N 29/46; G01F 1/666; G01F 1/7082
USPC ........... 73/24.01, 24.04, 24.06, 29.01, 29.05, 73/19.03, 19.04, 64.53
See application file for complete search history.

(56) References Cited

U.S. PATENT DOCUMENTS

| | | | |
|---|---|---|---|
| 4,193,290 A * | 3/1980 | Sustek et al. ................ | 73/24.04 |
| 4,679,947 A | 7/1987 | Miller et al. | |
| 5,148,405 A | 9/1992 | Belchamber et al. | |
| 5,353,627 A | 10/1994 | Diatschenko et al. | |
| 5,421,209 A | 6/1995 | Redus et al. | |
| 5,505,090 A | 4/1996 | Webster | |
| 5,756,898 A * | 5/1998 | Diatschenko et al. ......... | 73/592 |
| 6,293,156 B1 | 9/2001 | Shen et al. | |
| 6,581,466 B1 | 6/2003 | Costley et al. | |

(Continued)

OTHER PUBLICATIONS

International Search Report for PCT/US12/28113, International Searching Authority, Jun. 13, 2012, pp. 1-13.

(Continued)

*Primary Examiner* — Daniel S Larkin
*Assistant Examiner* — Jamar Ray
(74) *Attorney, Agent, or Firm* — Samuel M. Freund; Cochran Freund & Young LLC

(57) ABSTRACT

An apparatus and method for noninvasively monitoring steam quality and flow and in pipes or conduits bearing flowing steam, are described. By measuring the acoustic vibrations generated in steam-carrying conduits by the flowing steam either by direct contact with the pipe or remotely thereto, converting the measured acoustic vibrations into a frequency spectrum characteristic of the natural resonance vibrations of the pipe, and monitoring the amplitude and/or the frequency of one or more chosen resonance frequencies, changes in the steam quality in the pipe are determined. The steam flow rate and the steam quality are inversely related, and changes in the steam flow rate are calculated from changes in the steam quality once suitable calibration curves are obtained.

11 Claims, 6 Drawing Sheets

(56) References Cited

U.S. PATENT DOCUMENTS

| | | |
|---|---|---|
| 7,497,119 B2 | 3/2009 | Brooks et al. |
| 8,632,244 B2 * | 1/2014 | Bar-Cohen et al. .......... 374/117 |
| 2005/0011278 A1 | 1/2005 | Brown et al. |

OTHER PUBLICATIONS

Australian Patent Office Examination Report and firm letter from associate, Oct. 22, 2014, 6 pages.

* cited by examiner

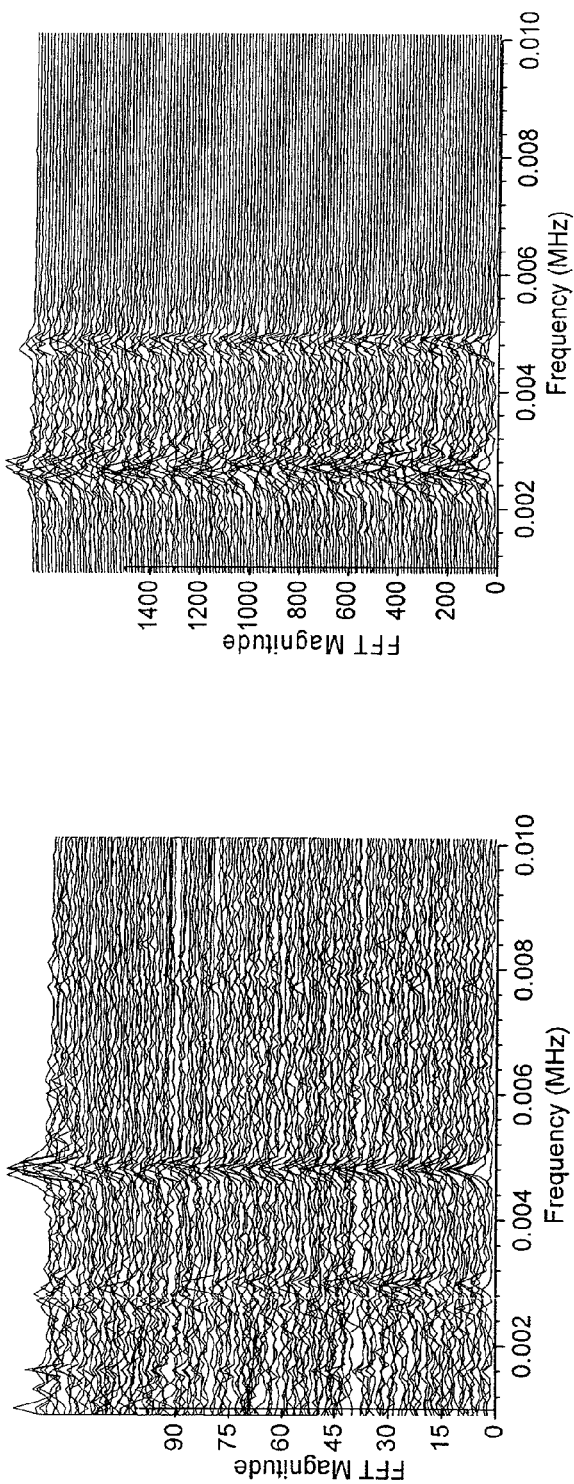
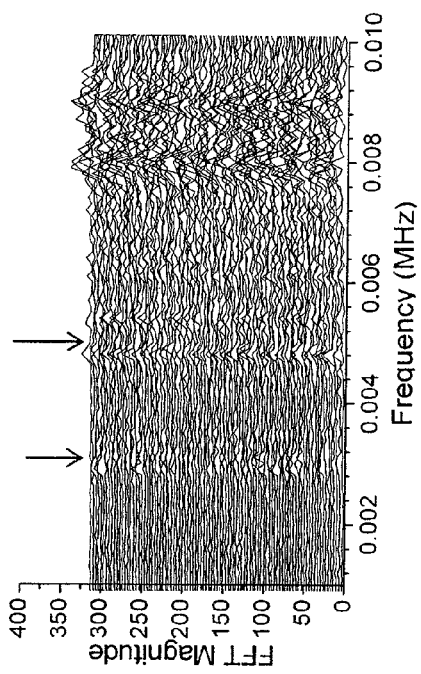
Fig. 2A
Fig. 2B
Fig. 2C

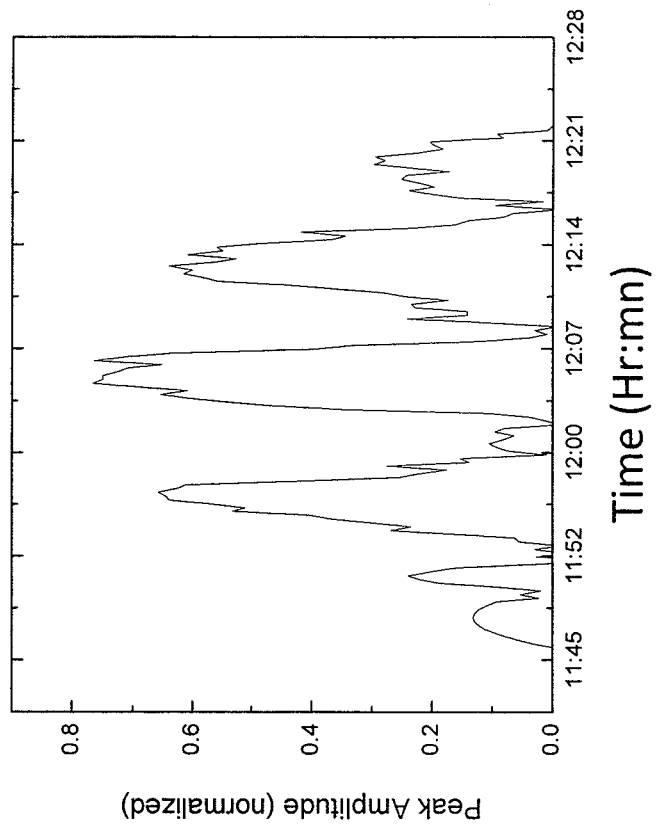
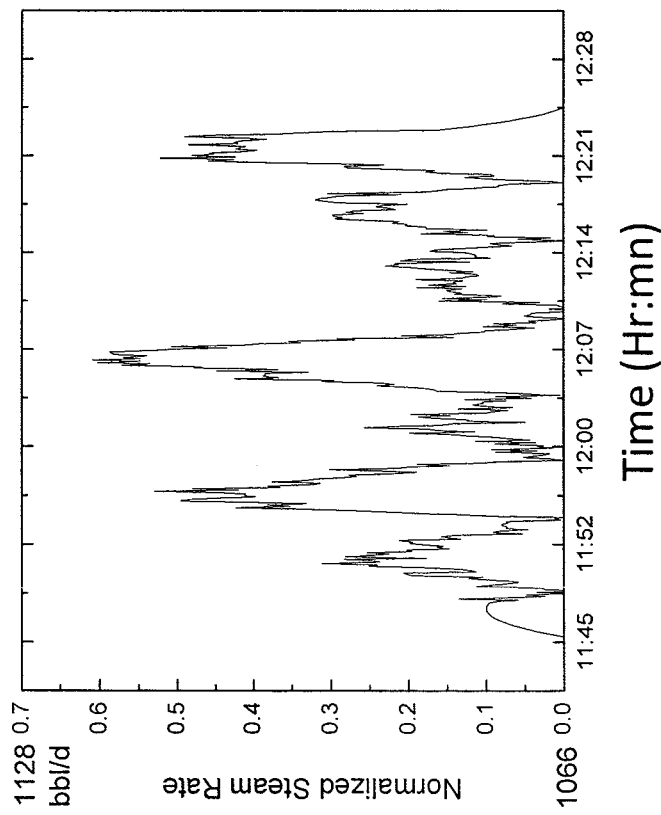
Fig. 3B
Fig. 3A

APPARATUS AND METHOD FOR ACOUSTIC MONITORING OF STEAM QUALITY AND FLOW

CROSS-REFERENCE TO RELATED APPLICATIONS

The present application claims the benefit of U.S. Provisional Patent Application No. 61/449,791 for "Method And Apparatus For Acoustic Steam Quality Monitoring" which was filed on Mar. 7, 2011, the entire contents of which is hereby specifically incorporated by reference herein for all that it discloses and teaches.

STATEMENT REGARDING FEDERAL RIGHTS

This invention was made with government support under Contract No. DE-AC52-06NA25396 awarded by the U.S. Department of Energy. The government has certain rights in the invention.

FIELD OF THE INVENTION

The present invention relates generally to oil recovery using steam and, more particularly to the noninvasive, real-time measurement of steam quality and flow.

BACKGROUND OF THE INVENTION

Heavy oil represents a substantial fraction of world petroleum reserves. Conventional production practices cannot recover a large percentage of this oil partly because high viscosity at reservoir conditions inhibits flow to production wells. Therefore, ultimate recovery by conventional production is frequently below 10%. Steam injection is the most widely utilized method for stimulating the production of heavy oil, currently accounting for approximately 80%. A benefit of using steam as a heat transfer medium is the large quantity of heat released when it condenses into water. With a latent heat of vaporization (or condensation) as high as 1,000 BTU per pound, very little steam carries a large quantity of energy. Other advantages include the safe, nontoxic and nonflammable characteristics of steam, in addition to its ability to deliver heat at a constant, controlled temperature.

Steam-flooding involves injection of two-phase steam having sufficient quality at effective rates into a reservoir. However, the cost for generating steam is high, accounting for about one-half of all steam-flooding operating costs. Because of the high steam cost and the difficulty in obtaining generator permits, optimization of the use of injected steam is necessary. However, the quality or steam delivered to the reservoir is largely unknown, which makes steam quality measurements important for both oil extraction and reservoir management. Such determinations are also important in other industries where steam is used.

Water can exist as either a gas or a liquid under saturated conditions. Wet steam can contain both gas and liquid components, known to those of ordinary skill in the art as two-phase flow. A common method of expressing the quantities of each phase, known as steam quality, is the ratio of the mass flow rate of the gas phase to the total mass flow rate, and is given as a number less than one, or as a percentage. Steam quality measurements, which are determinative of the efficiency of the steam delivery system in surface distribution lines, have been made using various methods. One technique is based on pressure drop measurements as the steam passes through an area constriction, and requires the accurate measurement of pressures with pressure measurement devices within the pipeline. Another method bleeds steam to the outside of a pipe through an orifice, for generating acoustic energy, which is detected. The amplitude of the detected signal is related to steam quality. However, this method produces unnecessary noise and releases steam into the environment. Capacitance measurements for determining steam quality, where the measurement apparatus is inserted into a steam carrying pipe, also requires an additional temperature or pressure measurement device. Measurements of differential pressure fluctuations on both sides of a metal plate containing an orifice inserted into a steam carrying pipe to determine steam quality also require pressure measurement devices connected through holes in the pipe.

Optical on-line measurement systems have been used as well for determining steam quality. Multiple wavelengths of radiant energy are passed through the steam from an emitter to a detector through optical windows in a pipe. By comparing the amount of radiant energy absorbed by the flow of steam for each wavelength, an accurate measurement of the steam quality can be determined on a continuous basis in real-time.

Since these approaches require either penetration of the steam-carrying pipes or insertion of devices into the pipe, none provides a simple and noninvasive method for monitoring steam quality that can be installed at one location and then readily moved to another location without significant plumbing changes, often rendering these methods unsuitable for field use. Additionally, steam conduits are operated in excess of 400° F., and measurement devices must withstand high temperatures.

Approximate measurements of steam flow rate or steam quality parameters, are often sufficient for field steam injection operations, and the ability to make noninvasive measurements at multiple locations using inexpensive, easily maintained and easily automated devices is of value.

SUMMARY OF THE INVENTION

Embodiments of the present invention overcome the disadvantages and limitations of the prior art by providing an apparatus and method for monitoring steam quality in real time.

Another object of embodiments of the present invention is to provide an apparatus and method for noninvasively monitoring steam quality in real time.

Yet another object of embodiments of the invention is to provide an apparatus and method for noninvasively monitoring steam quality at a chosen location along a steam pipe, and at other chosen locations along the pipe.

Still another object of embodiments of the present invention is to provide an apparatus and method for noninvasively monitoring steam flow in real time.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects, and in accordance with the purposes of the present invention, as embodied and broadly described herein, the method for monitoring steam quality at a chosen location in a pipe in which steam is flowing, hereof, includes the steps of: detecting sound generated in the pipe by the steam flowing through the pipe at the chosen location; determining at least one acoustic frequency from the natural resonance vibration frequency spectrum of the pipe; and monitoring a peak amplitude at the at least one acoustic vibration frequency; whereby changes in the steam quality are obtained from changes in the peak amplitude at the at least one acoustic vibration frequency.

In another aspect of the present invention and in accordance with its objects and purposes, the apparatus for monitoring steam quality at a chosen location in a pipe in which steam is flowing, hereof, includes: a piezoelectric transducer for detecting sound generated in the pipe by the steam flowing through the pipe at the chosen location; a signal processor for receiving the signal from the piezoelectric transducer and determining at least one acoustic frequency from the natural resonance vibration frequency spectrum of the pipe; and a microprocessor for monitoring a peak amplitude at the at least one acoustic vibration frequency from the signal processor; whereby changes in the steam quality are obtained from changes in the peak amplitude at the at least one acoustic vibration frequency.

In still another aspect of the present invention and in accordance with its objects and purposes, the apparatus for monitoring steam quality at a chosen location in a pipe in which steam is flowing, hereof, includes: a detector spaced-apart from the pipe for detecting sound generated in the pipe by the steam flowing through the pipe at the chosen location; a signal processor for receiving the signal from the detector and determining at least one acoustic frequency from the natural resonance vibration frequency spectrum of the pipe; and a microprocessor for monitoring a peak amplitude at the at least one acoustic vibration frequency from the signal processor; whereby changes in the steam quality are obtained from changes in the peak amplitude at the at least one acoustic vibration frequency.

In another aspect of the present invention and in accordance with its objects and purposes, the method for monitoring steam quality at a chosen location in a pipe in which steam is flowing, hereof, includes the steps of: detecting sound generated in the pipe by the steam flowing through the pipe at the chosen location; determining at least one acoustic frequency from the natural resonance vibration frequency spectrum of the pipe; and monitoring the frequency of a peak at the at least one acoustic vibration frequency; whereby changes in the steam quality are obtained from changes in the frequency of the peak at the at least one acoustic vibration frequency.

In another aspect of the present invention and in accordance with its objects and purposes, the apparatus for monitoring steam quality at a chosen location in a pipe in which steam is flowing, hereof, includes: a piezoelectric transducer for detecting sound generated in the pipe by the steam flowing through the pipe at the chosen location; a signal processor for receiving the signal from the piezoelectric transducer and determining at least one acoustic frequency from the natural resonance vibration frequency spectrum of the pipe; and a microprocessor for monitoring the frequency of a peak at the at least one acoustic vibration frequency from the signal processor; whereby changes in the steam quality are obtained from changes in the frequency of the peak at the at least one acoustic vibration frequency.

In yet another aspect of the present invention and in accordance with its objects and purposes, the apparatus for monitoring steam quality at a chosen location in a pipe in which steam is flowing, hereof, includes: a detector spaced-apart from said pipe for detecting sound generated in the pipe by the steam flowing through the pipe at the chosen location; a signal processor for receiving the signal from the detector and determining at least one acoustic frequency from the natural resonance vibration frequency spectrum of the pipe; and a microprocessor for monitoring the frequency of a peak at the at least one acoustic vibration frequency from the signal processor; whereby changes in the steam quality are obtained from changes in the frequency of the peak at the at least one acoustic vibration frequency.

Benefits and advantages of embodiments of the present invention include, but are not limited to, providing an apparatus and method for noninvasively monitoring steam quality and flow rate of steam flowing in a pipe from acoustic measurements made in direct contact with the pipe or remotely thereto. At certain frequencies, such acoustic measurements may be made through pipe insulation.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings:

FIG. 2A is a typical graph of the fast Fourier transform (FFT) of the sound emanating from a pipe containing flowing steam as a function of frequency obtained using a microphone; FIG. 2B is a typical graph of the fast Fourier transform of the sound in the wall of a pipe containing flowing steam as a function of frequency obtained using a transducer with a buffer rod; and FIG. 2C is a typical graph of the fast Fourier transform of the sound in the wall of a pipe containing flowing steam as a function of frequency obtained using a direct contact transducer.

FIG. 3A is a graph of the steam flow rate derived from pressure and temperature measurements as generated by a portable steam generator as a function of time, FIG. 3B is a graph of the output from a piezoelectric transducer coupled to the steam-carrying pipe by a buffer rod, as a function of time as the steam rate was varied between 1066 and 1128 bbl/day.

FIG. 4A is a graph of the steam rate (left ordinate) and the steam quality (right ordinate) as a function of time, qualitatively illustrating the inverse relationship between these two quantities; while

DETAILED DESCRIPTION OF THE INVENTION

When steam and, in particular wet steam, flows through a pipe, flow-induced vibrations are generated in the pipe at frequencies which range between the low audible to above normal hearing. As the steam quality changes, the generated frequency spectrum in the pipe varies with it. Embodiments of the present invention include an apparatus and method for noninvasively monitoring steam quality and flow in pipes and conduits bearing flowing steam. Measuring acoustic vibrations generated in steam-carrying conduits by the flowing steam either by direct contact with the pipe or remotely thereto, converting the measured acoustic vibrations into a frequency spectrum characteristic of the natural resonance vibrations of the pipe, and monitoring the amplitude and/or the resonance frequency of one or more chosen resonance peaks, permits changes in the flow rate of the steam in the pipe to be determined.

The steam quality and the steam flow rate are inversely related, as will be discussed in more detail hereinbelow, and as is set forth in Equation (9) of U.S. Pat. No. 5,421,209, which issued to Redus et al. on Jun. 6, 1995. Therefore, if either the steam quality or the steam flow rate is measured or otherwise known, the other is also known.

Figure 1:
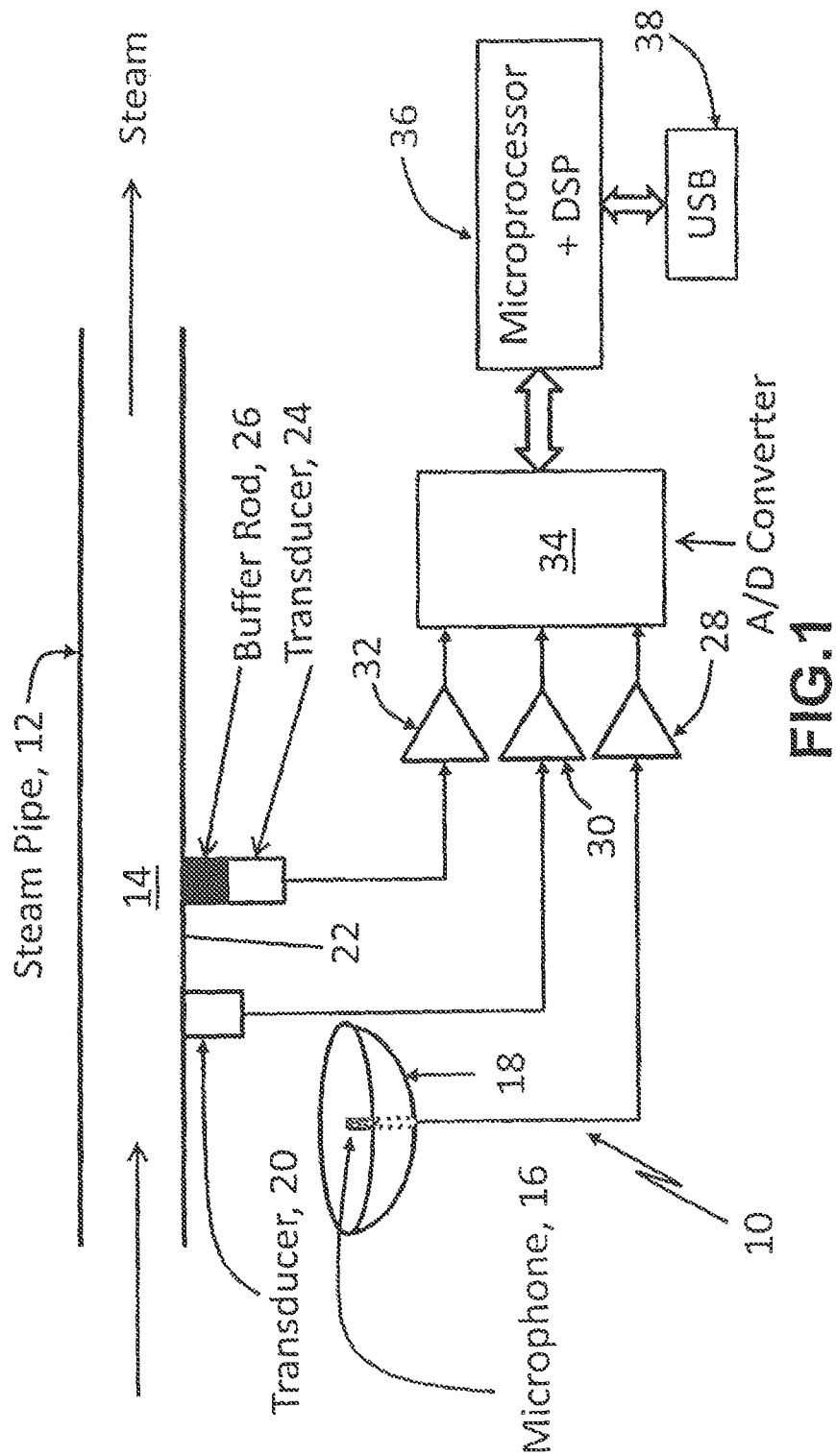
FIG. 1 is a schematic representation of embodiments of the apparatus of the present invention, illustrating the measurement of sound in a steam pipe using at least one of a microphone, an ultrasonic transducer separated from the pipe by a buffer rod, or an ultrasonic transducer placed in direct contact with the pipe.

Reference will now be made in detail to the present embodiments of the invention, examples of which are illustrated in the accompanying drawings. In the FIGURES, similar structure will be identified using identical reference characters. It will be understood that the FIGURES are for the purpose of describing particular embodiments of the invention and are not intended to limit the invention thereto. Turning now to FIG. 1, embodiments, 10, of the present invention for permitting the detection of vibrations in steam pipe, 12, carrying flowing steam, 14, are shown. Broadband (100 Hz-120 kHz), pencil-type microphone, 16, having −49 dB sensitivity, and spaced apart from pipe 12, was used to detect the sound in air emanating from pipe 12 at a distance of 2 in. without using a sound collection device. A low bandwidth (~100 Hz-10 kHz) microphone would be effective for this purpose. Parabolic reflector, 18, can further enhance the detection capability and increase the stand-off distance to ~100 ft. Microphone 16 can be placed within a few inches (>2 in.) of pipe 12 to avoid the effects of the heat of steam-carrying pipe 12. Microphone 16 is useful for scanning a length of a pipe or examining many locations in a steam generation facility quickly without having to install a device onto any of the pipes. When steam-carrying pipes are closely packed, it may be useful to bring the microphone closer to a particular pipe so that signals from adjoining pipes do not interfere with the measurements. A directional microphone or a phased-array microphone system having greater directionality than a single microphone may useful in such interference situations. A phased-array system includes multiple microphones arranged in a periodic pattern and allows electronic aiming over a wider region of the pipe without moving the sensor as in the case of the parabolic receiver or the directional microphone.

Other suitable commercially available stand-off vibration detectors include fiber optic systems, laser Doppler vibrometers, and capacitance and electromagnetic sensors.

Direct contact vibration detection measurements were used to verify the stand-off detector measurements. Since the surface of pipe 12 is hot (>400° F.), disc-shaped, lithium niobate piezoelectric crystal (1 MHz center frequency, 5 mm diameter), 20, was coupled directly to pipe surface, 22, as a vibration detector. Lithium niobate has a long lifetime at such temperatures, while bismuth titanate piezoelectric ceramics may be used for direct-contact measurements at operating temperatures up to 800° F. As an alternative, piezoelectric transducer (lead zirconate-lead titanate) disc (500 kHz center frequency), 24, having cylindrical quartz buffer rod (5 mm diameter and 1 cm long), 26, was inserted between transducer 24 and pipe surface 22. Quartz has a low thermal conductivity and thus provides good temperature insulation for protecting the piezoelectric crystals. However, even with the use of buffer rod 26, the piezoelectric vibration detector is not suitable for long-term usage at temperatures above 400° F. because of deterioration of piezoelectric properties. A circulating fluid heat sink (not shown in FIG. 1) may used to enhance crystal lifetimes. Piezoelectric disc 24 was back-loaded with tungsten-loaded epoxy to broaden its frequency response. Other ultrasonic transducers having the requisite frequency bandwidth can be used as well. For detecting vibrations, lithium niobate crystal 20 or transducer-buffer rod assembly 24, 26 need only make physical contact under slight pressure with pipe surface 22 to achieve acoustic coupling with pipe 12; no coupling gel is needed. A mechanical fixture (not shown in FIG. 1) for holding the transducer-rod system against the pipe is adequate for the present measurements.

As stated, it may not be necessary to make measurements where thermal insulation on the steam-carrying pipe is removed in order to provide access to the vibration measurement sensors, since frequencies less than 10 kHz transmit well through such insulation without much attenuation.

Direct contact vibration measurements are especially useful when there are too many pipes carrying steam, the valves or pipe sections are very close to each other, thereby preventing installation of stand-off measurement devices, or vibration measurements from a particular region of interest. Since there is no requirement for coupling gels or epoxies, transducers can be easily removed and moved to another location.

Signals from either the microphone or the contact measurement transducers are first amplified using amplifiers, 28, 30, and 32, respectively, and then directed to multi-channel, 12-bit, 100 kHz bandwidth A/D converter, 34. If measurements from multiple locations are required, the present system can easily be expanded to 32 or more separate channels. Microprocessor, 36, having an integral or separate DSP (digital signal processor), analyzes the signal from each channel and provides an output, such as USB or Ethernet, 38. The DSP system is sufficiently fast to process the signal from a phased-array microphone system. A FFT (Fast Fourier Transform) of the digitized vibration data is performed by the DSP in less than 100 µs, and determines the vibration frequency spectrum. These vibration frequencies are related to the various natural resonance frequencies of pipe (conduit) 12 that are excited by the flow of steam through the pipe. The steam interacts with the pipe surface as it flows, transferring molecular energy possessed by steam to the pipe surface which in turn excites and amplifies the natural frequencies of the pipe that are detected in accordance with embodiments of the present invention. At high flow rates, the turbulent nature of the flow also enhances this energy coupling to the pipe due to vortex shedding, and other coupling phenomena. The mechanisms giving rise to such flow-induced vibrations have been extensively studied and are well understood. The amplitudes and also the resonance peak frequencies of various resonance frequencies are therefore related to the steam flow rate and to the steam quality. The amplitude of the peak may be a better indicator since it is more easily measured. The output can be in a variety of forms such as graphs, numbers displayed on an LCD screen, an alarm signal when identified ranges of steam quality are exceeded, or input to an appropriate feedback control, whereby a choke valve may be adjusted to control steam flow.

A spectrum analyzer may be employed for directly providing a frequency spectrum that can be used to track resonance peaks and their amplitudes on a microprocessor.

FIGS. 2A, 2B, and 2C are graphs of the FFT magnitude as a function of frequency from the stand-off microphone, the piezoelectric transducer and the buffer rod/piezoelectric transducer combination, respectively, from simultaneous measurements for comparison purposes. The frequency spectra are obtained using FFT processing in the DSP of the recorded vibration amplitude data in real time. The data are plotted as a water-fall to display the variation of the spectra as a function of time as steam passes through the pipe. Steam was obtained from a portable steam generator on a trailer that was positioned approximately 100 feet from the measurement location. The steam rate and the steam quality values were also obtained for this portable steam generator. The three measurements provide almost identical results in terms of their frequency spectrum. For example, the peaks in the FFT spectra around 3 and 5 kHz are observed in all measurements, and are in fact the pipe resonances excited by the flow and quality of steam as mentioned hereinabove. The direct contact lithium niobate crystal measurement also shows the two peaks around 3 and 5 kHz in addition to stronger peaks (higher amplitude) around 8 and 9 kHz which are a result of the increased sensitivity of the lithium niobate transducer at higher frequencies. The frequency locations of these peaks are related to the pipe dimensions (diameter, wall thickness, and pipe material) and the frequency peaks (shown in FIG. 2) are specific to these particular measurements and configuration. Pipes having different geometries or dimensions will have different resonance characteristics. For a given type of steam carrying pipe (typically these are standard pipes and used almost universally) there will be associated resonance peaks and one may monitor the amplitude of these frequencies. Most resonance peaks can be used for the steam quality measurements, although the sensitivity may vary somewhat from peak to peak. The amplitudes and/or frequencies of these peaks can be correlated with steam flow rate and the steam quality as these are inversely related as mentioned hereinabove and illustrated hereinbelow, once calibration curves are generated. The data show that the frequency content of the pipe vibration is more pronounced when the frequency is less than approximately 10 kHz; however, this may vary based on the pipe dimensions. For the present measurements, 25 kHz was used as an upper frequency cut off value since little vibration activity was found above that frequency. The results presented in FIG. 2 clearly show that both stand-off and direct contact vibration measurements provide the same flow-induced pipe resonance frequency information.

Figure 3C:
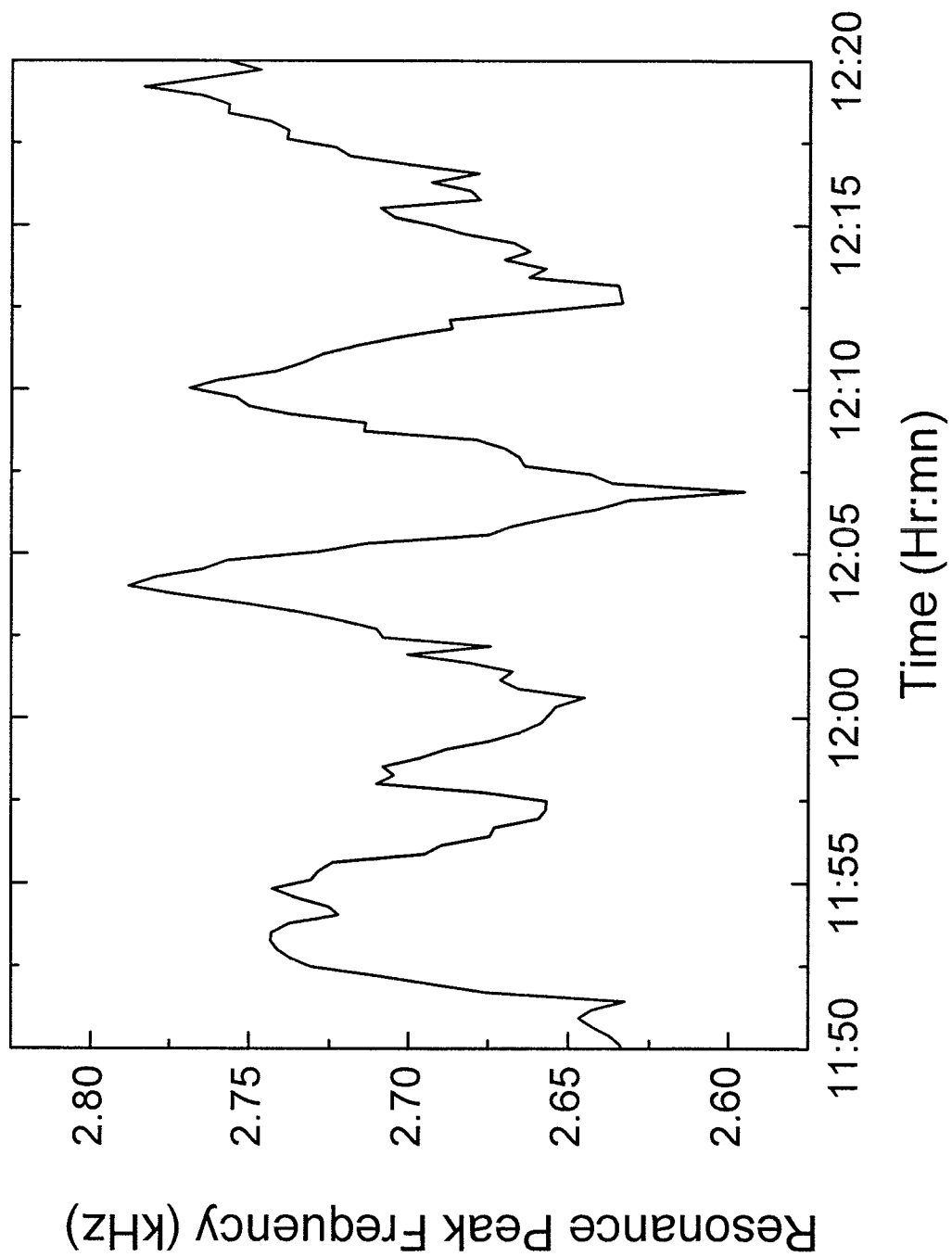
FIG. 3C is a graph of resonance peak frequency as a function of time (steam flow rate) for a single resonance peak.

FIGS. 3A and 3B compare the steam rate produced by the portable steam generator (derived from pressure and temperature measurements) and the measurement obtained from the piezoelectric crystal-buffer rod combination. Measurements from the microphone and the lithium niobate crystal show similar results consistent with the discussion presented hereinabove. For this measurement, the 5 kHz resonance peak was arbitrarily chosen, and its amplitude was monitored. Measurements (normalized) are shown for a period of approximately 40 min. when the steam rate varied between 1066 to 1128 bbl/day. This small change in steam rate corresponds to an approximate variation of 2% in steam quality (74-76%). The steam quality follows the inverse of the steam rate as provided by this portable steam generator. This small range illustrates the sensitivity of the present method. The correlation between the acoustic based noninvasive measurement and the actual value produced by the steam generator are in excellent agreement (FIGS. 3A and 3B) where the variations in the acoustic data and the steam rate value show near identical behavior. The exact steam rate at the location of the measurement is expected to be slightly different from that produced at the steam generator located almost 100 ft. away, and therefore one does not expect a perfect correlation between the two measurements. The strong observed correlation, however, indicates that the flow-induced resonance vibration induced in the steam-carrying pipe can indeed be used for steam rate or steam quality measurements. For larger variations in steam rate, the variations in the resonance peak amplitudes and frequency shifts are expected to be much larger. In such situations, it is easier to track the frequency that corresponds to any resonance peak and these may be used for steam quality and steam rate measurement as well. FIG. 3C shows data for resonance peak frequency shifts with changes in steam flow rate for a single resonance peak at ~2.6 kHz. The frequency shift is small in this case since the variation in the steam flow rate was determined to be small. As discussed in part, hereinabove, the shift in resonance frequency occurs as a result of flow coupling with the pipe surface and Doppler shift. Therefore, either the peak frequency location of any observed pipe resonance peak or its amplitude may be used for the measurement that is correlated with steam quality or steam flow rate. For higher quality data, signal averaging is advantageous. For peak frequency position tracking, a narrow band-pass filter may be used to reduce fluctuations in the data. The DSP and the microprocessor shown in FIG. 1 perform data smoothing and data filtering in real-time.

Figure 4A:
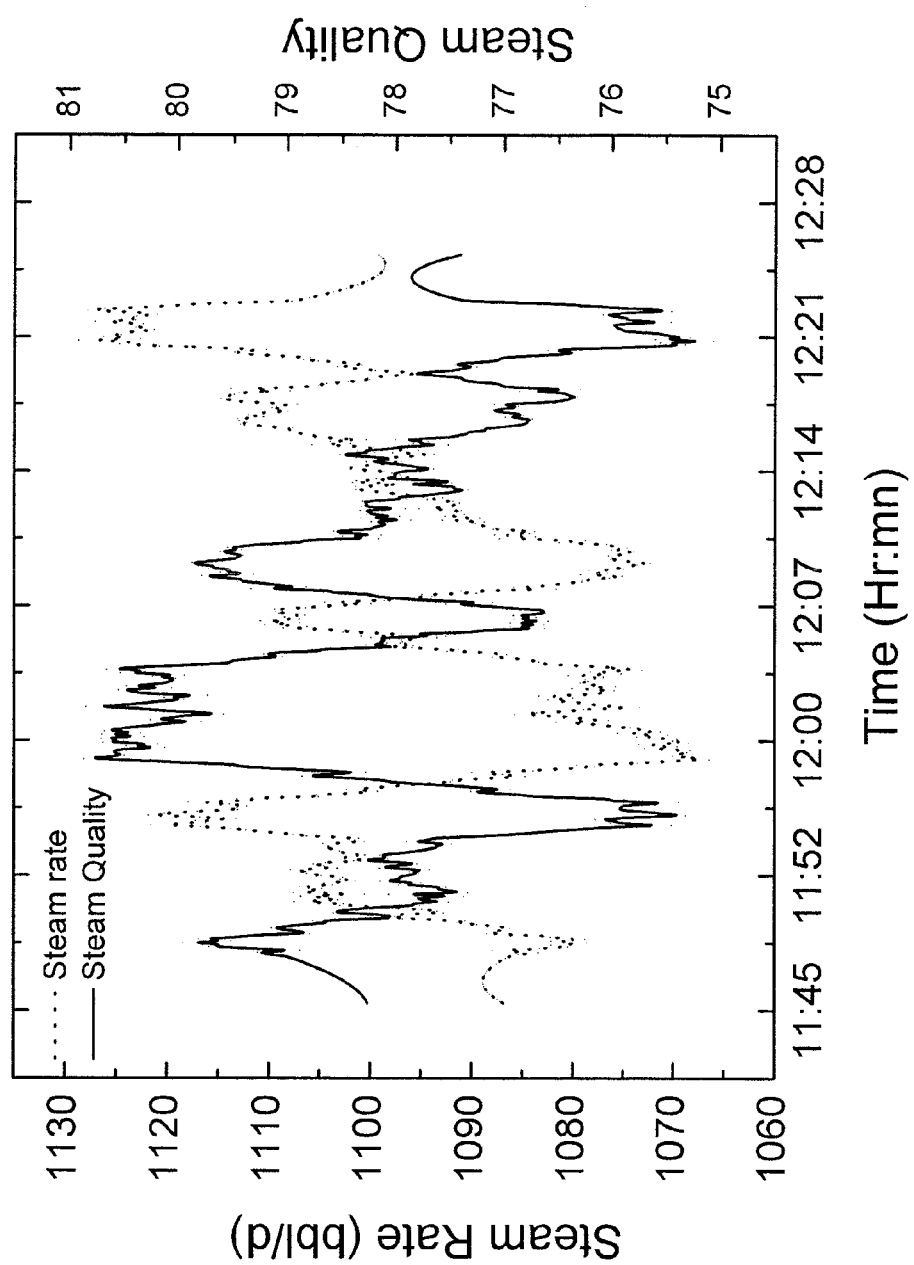
Figure 4B:
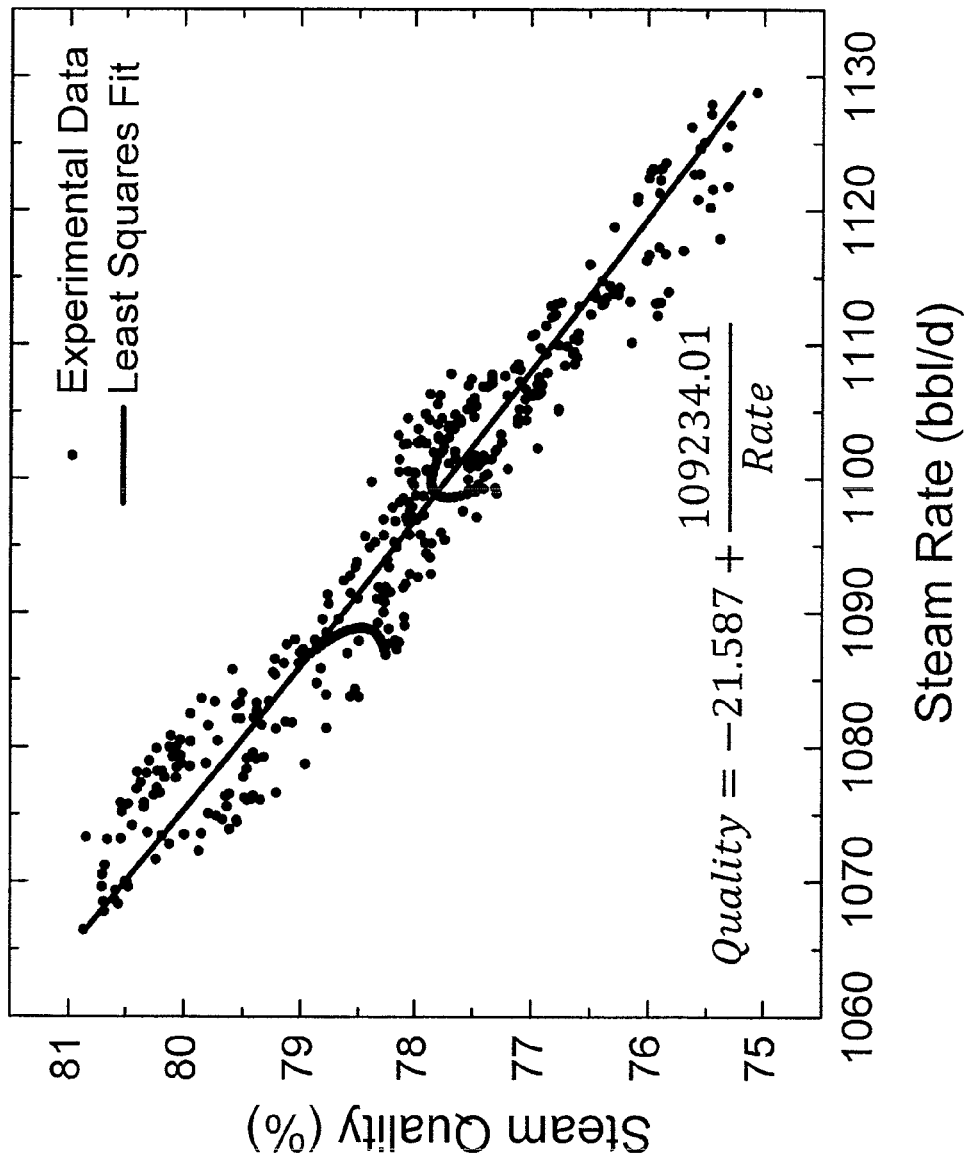
FIG. 4B is a graph showing a least-squares fit of steam quality data as a function of steam flow rate, quantitatively illustrating the inverse relationship between these two quantities.

FIGS. 4A and 4B show the relationship between steam flow rate and steam quality. The measurements are generated by the portable steam generator based on thermodynamic measurements of pressure and temperature. FIG. 4A shows that these two measurements are inversely related as one is an inverted version of the other, while FIG. 4B is a graph of steam flow rate as a function of steam quality. The solid circles in the plot are actual measurements and the solid line is a least-squares fit of the data. This fit can be represented by a simple equation as Steam Quality=−21.587+ 109234.01/Steam Flow Rate. Therefore, measurement of one parameter provides a measurement for the other, and the present acoustic measurements are related to both parameters.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for monitoring steam quality at a chosen location in a pipe in which steam is flowing, comprising the steps of:

detecting sound generated in the pipe by the steam flowing through the pipe at the chosen location;

selecting at least one acoustic frequency from a natural resonance vibration frequency spectrum of the pipe responsive to the flow of steam, and comprising at least one resonance frequency; and monitoring the peak amplitude at the at least one acoustic vibration frequency;

whereby changes in the steam quality are obtained from changes in the peak amplitude at the at least one acoustic vibration frequency.

2. The method of claim 1, further comprising the step of calculating the change in steam flow rate from the change in steam quality.

3. The method of claim 1, wherein said step of detecting sound generated in the pipe is achieved using a microphone.

4. The method of claim 3, wherein the microphone comprises a parabolic reflector.

5. The method of claim 3, wherein the microphone is chosen from a pencil microphone, a directional microphone and a phased-array microphone.

6. The method of claim 1, wherein said step of detecting sound generated in the pipe is achieved using a laser Doppler vibrometer.

7. The method of claim 1, wherein said step of detecting sound generated in the pipe is achieved using a piezoelectric transducer in acoustic contact with the pipe.

8. The method of claim 7, wherein the piezoelectric transducer is chosen from lithium niobate, lead zirconate-lead titanate and bismuth titanate crystals.

9. The method of claim 1, wherein said step of detecting sound generated in the pipe is achieved using a piezoelectric transducer in acoustic contact with a buffer rod in acoustic contact with the pipe.

10. The method of claim 9, wherein the piezoelectric transducer is chosen from lithium niobate, lead zirconate-lead titanate, and bismuth titanate crystals.

11. The method of claim 1, further comprising the step of generating a fast Fourier transform of the detected sound generated in the pipe.

\* \* \* \* \*